United States Patent
Larisch (10) Patent No.: US 7,423,115 B2
(45) Date of Patent: Sep. 9, 2008

(54) ARTS C-TERMINUS FRAGMENTS AND MIMETICS THEREOF

(75) Inventor: Sarit Larisch, Zichron-Yaakov (IL)

(73) Assignee: SimeTRA Pharm Ltd, Kiryat Shomona (IL)

( * ) Notice: Subject to any disclaimer, the term of this patent is extended or adjusted under 35 U.S.C. 154(b) by 0 days.

(21) Appl. No.: 11/439,192

(22) Filed: May 24, 2006

(65) Prior Publication Data

US 2006/0270601 A1    Nov. 30, 2006

Related U.S. Application Data

(60) Provisional application No. 60/684,174, filed on May 25, 2005.

(51) Int. Cl.
| | | |
|---|---|---|
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |

(52) U.S. Cl. ..................... 530/328; 530/332
(58) Field of Classification Search ........... None
See application file for complete search history.

(56) References Cited

U.S. PATENT DOCUMENTS

2005/0227302 A1* 10/2005 Larisch et al. ............ 435/7.23

OTHER PUBLICATIONS

Kieber-Emmons, T., Murali, R., and Greene, M.I. Therapeutic peptides and peptidomimetics. Current Opinion in Biotechnology, 1997. vol. 8, pp. 435-441.*

Hruby, V.J. and Balse, P.M. Conformational and topographical considerations in designing agonist peptidomimetics from peptide leads. Current Medicinal Chemistry, 2000. vol. 7, pp. 945-970.*

Larisch, Lotan, Kerner, Eimeri, Parks, Gottfried, Reffey, De Caestecker, Danielpour, Book-Melamed, Timberg, Duckett, Lechleider, Steller, Orley, Kim and Roberts. A novel mitochondrial septin-like protein, ARTS, mediates apoptosis dependent on its P-loop motif. Nature Cell Biology, 2000. vol. 2, pp. 915-921.*

Gottfried, Y., Rotem, A., Lotan, R., Steller, H., and Larisch, S. The mitochondrial ARTS protein promotes apoptosis through targeting XIAP. EMBO Journal, 2004. vol. 23, pp. 1627-1635.*

* cited by examiner

*Primary Examiner*—Larry R. Helms
*Assistant Examiner*—Anne M Gussow
(74) *Attorney, Agent, or Firm*—Pearl Cohen Zedek Latzer, LLP (57) ABSTRACT

This invention provides isolated peptides comprising a C-terminal fragment of an ARTS protein, isolated nucleotides encoding same, mimetics and small molecule analogues of same, and therapeutic applications comprising administering a peptide, nucleic acid, or mimetic compound of the present invention. This invention also provides isolated complexes comprising a C-terminal fragment of an ARTS protein and either an IAP protein, a Bir3 domain thereof, or a fragment thereof; compounds that bind or interact with same, and use of the compounds in therapeutic applications.

2 Claims, 3 Drawing Sheets

Figure 3 ured by this application Ser. No. 60/684,174, filed May 25, 2005. This application is hereby incorporated in its entirety by reference herein.

ARTS C-TERMINUS FRAGMENTS AND MIMETICS THEREOF

CROSS REFERENCE TO RELATED APPLICATION

This application claims priority of U.S. Provisional Application Ser. No. 60/684,174, filed May 25, 2005. This application is hereby incorporated in its entirety by reference herein.

FIELD OF INVENTION

This invention provides isolated peptides comprising a C-terminal fragment of an ARTS protein, isolated nucleotides encoding same, mimetics and small molecule analogues of same, and therapeutic applications comprising administering a peptide, nucleic acid, or mimetic compound of the present invention. This invention also provides isolated complexes comprising a C-terminal fragment of an ARTS protein and either an IAP protein, a Bir3 domain thereof, or a fragment thereof; compounds that bind or interact with same, and use of the compounds in therapeutic applications.

BACKGROUND OF THE INVENTION

Programmed cell death by apoptosis is a major mechanism for regulating cell number and tissue homeostasis. Apoptosis is tightly controlled through the action of both activators and inhibitors of caspases. One family of caspase inhibitors is the Inhibitors of Apoptosis Proteins (IAP). IAP contain 1-3 baculoviral IAP repeat (BIR) domains, which directly interact with caspases and inhibit their apoptotic activity. XIAP is an IAP protein.

ARTS is a pro-apoptotic protein derived by differential splicing from the human septin H5/PNUTL2/CDCrel-2a (Sept4) gene. ARTS contains a P-loop GTP-binding motif conserved in the Sept family. Yet unlike most other Sept family members, it is localized to mitochondria and promotes apoptosis via TGF-beta and other pro-apoptotic stimuli, such as etoposide, arabinoside (ara-C), staurosporine and Fas. A number of types of cancer and neoplastic cells lack ARTS protein expression and/or activity.

Methods for inducing apoptosis in cells, for example neoplastic or cancer cells, are needed for therapeutic applications for a wide range of diseases. In addition, methods for inhibiting excessive or aberrant apoptosis in cells are needed for therapeutic applications for a different major class of diseases.

SUMMARY OF THE INVENTION

This invention provides isolated peptides comprising a C-terminal fragment of an ARTS protein, isolated nucleotides encoding same, mimetics and small molecule analogues of same, and therapeutic applications comprising administering a peptide, nucleic acid, or mimetic compound of the present invention. This invention also provides isolated complexes comprising a C-terminal fragment of an ARTS protein and either an IAP protein, a Bir3 domain thereof, or a fragment thereof; compounds that bind or interact with same, and use of the compounds in therapeutic applications.

In one embodiment, the present invention provides a mimetic compound of an ARTS (Apoptosis Related Protein in the TGF-β Signaling Pathway) protein C terminus. In another embodiment, the compound is a mimetic of a fragment of the ARTS C terminus. Each possibility represents a separate embodiment of the present invention.

In another embodiment, the present invention provides a method of inducing an apoptosis or a killing of a cell, comprising administering to the cell a mimetic compound of the present invention.

In another embodiment, the present invention provides a method of enhancing a sensitivity of a cell to a pro-apoptotic stimulus, comprising administering to the cell a mimetic compound of the present invention.

In another embodiment, the present invention provides a method of enhancing an effectiveness of cancer chemotherapy, comprising administering to a cancer cell a mimetic compound of the present invention.

In another embodiment, the present invention provides a method of inhibiting an apoptosis or a killing of a cell, comprising administering to the cell a mimetic compound of the present invention.

In another embodiment, the present invention provides a method of treating a disease or disorder, wherein the disease or disorder comprises a lack of responsiveness of a somatic cell to a pro-apoptotic stimulus, comprising administering to the somatic cell a mimetic compound of the present invention.

In another embodiment, the present invention provides a method of treating a disease or disorder, wherein the disease or disorder comprises an excessive apoptosis of a somatic cell, comprising administering to the somatic cell a mimetic compound of the present invention. In another embodiment, the disease or disorder comprises an inappropriate apoptosis of a somatic cell.

In another embodiment, the present invention provides an isolated complex comprising a C-terminal fragment of an ARTS protein and an IAP protein or a fragment of the IAP protein.

In another embodiment, the present invention provides a compound that selectively binds to an isolated complex of the present invention.

In another embodiment, the present invention provides a compound that inhibits a formation of an isolated complex of the present invention.

In another embodiment, the present invention provides a compound that disrupts an isolated complex of the present invention.

In another embodiment, the present invention provides a method of testing a compound for an ability to inhibit or reduce an incidence of an apoptosis, comprising determining whether the compound disrupts an isolated complex of the present invention, whereby if the compound disrupts an isolated complex of the present invention, then the compound inhibits or reduces an incidence of an apoptosis.

In another embodiment, the present invention provides a method of enhancing an effectiveness of cancer chemotherapy, comprising administering to a cancer cell a compound that promotes a formation of an isolated complex of the present invention, wherein the cancer cell is a target of the cancer chemotherapy.

In another embodiment, the present invention provides a method of testing a compound for an ability to inhibit or reduce an apoptosis, comprising determining whether the compound inhibits a binding of a C-terminal fragment of an ARTS protein to an XIAP protein, whereby if the compound inhibits binding of the C-terminal fragment of an ARTS protein to the IAP protein, then the compound inhibits or reduces an incidence of an apoptosis.

In another embodiment, the present invention provides a method of testing a compound for an ability to increase or potentiate an apoptosis, comprising determining whether the compound enhances a binding of a C-terminal fragment of an ARTS protein to an IAP protein, whereby if the compound enhances binding of the C-terminal fragment of an ARTS protein to the IAP protein, then the compound increases or potentiates an apoptosis.

In another embodiment, the present invention provides a method of testing a compound for an ability to enhance an effectiveness of a cancer chemotherapy, comprising determining whether the compound enhances a binding of a C-terminal fragment of an ARTS protein to an IAP protein, whereby if the compound enhances binding of the C-terminal fragment of an ARTS protein to the IAP protein, then the compound enhances an effectiveness of a cancer chemotherapy.

DETAILED DESCRIPTION OF THE INVENTION

This invention provides isolated peptides comprising a C-terminal fragment of an ARTS protein, isolated nucleotides encoding same, mimetics and small molecule analogues of same, and therapeutic applications comprising administering a peptide, nucleic acid, or mimetic compound of the present invention. This invention also provides isolated complexes comprising a C-terminal fragment of an ARTS protein and either an IAP protein, a Bir3 domain thereof, or a fragment thereof; compounds that bind or interact with same, and use of the compounds in therapeutic applications.

In one embodiment, the present invention provides a mimetic compound of an ARTS protein C terminus. In another embodiment, the compound is a mimetic of a portion of the ARTS C terminus. Each possibility represents a separate embodiment of the present invention.

In another embodiment, a mimetic compound of the present invention is a small molecule. "Small molecule" refers, in another embodiment, to a molecule with a molecular weight (MW) of less than 1000 daltons. In another embodiment, the MW is less than 900 daltons. In another embodiment, the MW is less than 800 daltons. In another embodiment, the MW is less than 700 daltons. In another embodiment, the MW is less than 600 daltons. In another embodiment, the MW is less than 500 daltons. In another embodiment, the MW is less than 400 daltons. In another embodiment, the MW is less than 350 daltons. In another embodiment, the MW is less than 300 daltons. In another embodiment, the MW is less than 250 daltons. In another embodiment, the MW is less than 200 daltons. Each possibility represents a separate embodiment of the present invention.

In another embodiment, the mimetic compound is a non-peptide compound. In another embodiment, the mimetic compound is a peptide-based compound. In another embodiment, the mimetic compound is any other type of compound known in the art. Each possibility represents a separate embodiment of the present invention.

"ARTS C terminus" refers, in another embodiment, to the 27 C terminal amino acids (AA) of an ARTS protein. In another embodiment, the ARTS protein has the sequence set forth in SEQ ID No: 4. In another embodiment, "ARTS C terminus" refers to the 27 C-terminal AA of a protein homologous to the sequence set forth in SEQ ID No: 4. In another embodiment, the term refers to the AA sequence set forth in SEQ ID No: 1. In another embodiment, the term refers an AA sequence homologous to the sequence set forth in SEQ ID No: 1. Each possibility represents a separate embodiment of the present invention.

In another embodiment, the portion of the ARTS C-terminus used to design the mimetic compound is at least 3 AA long. In another embodiment, the portion is at least 4 AA long. In another embodiment, the portion is at least 5 AA long. In another embodiment, the portion is at least 6 AA long. In another embodiment, the portion is at least 7 AA long. In another embodiment, the portion is at least 8 AA long. In another embodiment, the portion is at least 9 AA long. In another embodiment, the portion is at least 10 AA long. In another embodiment, the portion is at least 11 AA long. In another embodiment, the portion is at least 12 AA long. In another embodiment, the portion is at least 13 AA long. In another embodiment, the portion is at least 14 AA long. In another embodiment, the portion is at least 15 AA long. In another embodiment, the portion is at least 16 AA long. In another embodiment, the portion is at least 17 AA long. In another embodiment, the portion is at least 18 AA long. In another embodiment, the portion is at least 19 AA long. In another embodiment, the portion is at least 20 AA long. In another embodiment, the portion is at least 21 AA long. In another embodiment, the portion is at least 22 AA long. In another embodiment, the portion is at least 23 AA long. In another embodiment, the portion is at least 24 AA long. In another embodiment, the portion is at least 25 AA long. In another embodiment, the portion is at least 26 AA long. Each possibility represents a separate embodiment of the present invention.

In another embodiment, the portion of the ARTS C-terminus is 6 AA long. In another embodiment, the portion is 7 AA long. In another embodiment, the portion is 8 AA long. In another embodiment, the portion is 9 AA long. In another embodiment, the portion is 10 AA long. In another embodiment, the portion is 11 AA long. In another embodiment, the portion is 12 AA long. In another embodiment, the portion is 13 AA long. In another embodiment, the portion is 14 AA long. In another embodiment, the portion is 15 AA long. In another embodiment, the portion is 16 AA long. In another embodiment, the portion is 17 AA long. In another embodiment, the portion is 18 AA long. In another embodiment, the portion is 19 AA long. In another embodiment, the portion is 20 AA long. In another embodiment, the portion is 21 AA long. In another embodiment, the portion is 22 AA long. In another embodiment, the portion is 23 AA long. In another embodiment, the portion is 24 AA long. In another embodiment, the portion is 25 AA long. In another embodiment, the portion is 26 AA long. Each possibility represents a separate embodiment of the present invention.

In another embodiment, the ARTS protein of methods and compositions of the present invention has a sequence as set forth in SEQ ID No: 4. In another embodiment, the ARTS protein is homologous to the sequence set forth in SEQ ID No: 4:

(SEQ ID No: 4)
MIKRFLEDTTDDGELSKFVKDFSGNASCHPPEAKTWASRPQVPEPRPQAP

DLYDDDLEFRPPSRPQSSDNQQYFCAPAPLSPSARPRSPWGKLDPYDSSE

DDKEYVGFATLPNQVHRKSVKKGFDFTLMVAGESGLGKSTLVNSLFLTDL

YRDRKLLGAEERIMQTVEITKHAVDIEEKGVRLRLTIVDTPGFGDAVNNT

ECWKPVAEYIDQQFEQYFRDESGLNRKNIQDNRVHCCLYFISPFGHGYGP

SLRLLAPPGAVKGTGQEHQGQGCH.

In another embodiment, the C-terminal fragment of an ARTS protein has the sequence: YGPSLRLLAPPGAVKGT-GQEHQGQGCH (SEQ ID No: 1). In another embodiment, the ARTS C terminus is homologous to the sequence set forth in SEQ ID No: 1. Each possibility represents a separate embodiment of the present invention. In another embodiment, the C-terminal ARTS fragment is a C-terminal fragment of a protein having an AA sequence selected from those set forth in GenBank Accession numbers NM_004574, NM_080416, NM_080415, and BC018056. Each possibility represents a separate embodiment of the present invention.

Mimetic compounds of the present invention are derived, in another embodiment, from an ARTS fragment that is capable of performing a specified biological function. In another embodiment, the compounds are derived from the smallest portion of the ARTS C terminus that retains the described activity. In another embodiment, the compounds are derived from the smallest portion of the ARTS C terminus that retains a biological activity exhibited by the full-length protein. In another embodiment, a mimetic compound of the present invention exhibits a biological function exhibited by an ARTS protein. In another embodiment, a mimetic compound of the present invention exhibits a biological function exhibited by an ARTS C terminus. Each possibility represents a separate embodiment of the present invention.

In another embodiment, the portion of the ARTS protein C-terminal sequence is a minimum region of the C-terminal fragment that is capable of performing a specified biological function. In another embodiment, "minimum region" refers to the smallest portion of the C terminal fragment that retains the described activity. In another embodiment, "minimum region" refers to the smallest portion of the C terminal fragment that retains a biological activity exhibited by the full-length protein. In another embodiment, the "minimum region" does not exactly define the smallest portion of the C terminal fragment that exhibits the property, but rather approximately defines it.

In another embodiment, "biological activity" refers to an apoptosis. In another embodiment, "biological activity" refers to a killing of a cancer cell. In another embodiment, "biological activity" refers to an activity against a psoriasis. In another embodiment, "biological activity" refers to an activity against a tuberculosis infection. In another embodiment, "biological activity" refers to an activity against a Bartonella infection. In another embodiment, "biological activity" refers to an activity against a vitiligo. In another embodiment, "biological activity" refers to an activity against an atopic dermatitis. In another embodiment, "biological activity" refers to an activity against a hyper-proliferative dermatosis. In another embodiment, "biological activity" refers to an activity against a UV-responsive dermatosis. In another embodiment, "biological activity" refers to an activity against a lymphohistiocytosis.

In another embodiment, "biological activity" refers to a binding to an IAP protein. In another embodiment, "biological activity" refers to a release of a caspase from an IAP protein. In another embodiment, the IAP protein is an XIAP protein. In another embodiment, the IAP protein is a CIAP protein. In another embodiment, the IAP protein is any other IAP protein known in the art. Each possibility represents a separate embodiment of the present invention.

In another embodiment, the present invention provides a method of inducing an apoptosis or a killing of a cell, comprising administering a mimetic compound of the present invention. In another embodiment, the mimetic compound exhibits a biological characteristic of an ARTS C-terminal fragment. Such mimetic compounds exhibit, in another embodiment, an ability to induce apoptosis or killing of a cell in a similar manner to the ARTS C-terminal fragment.

In another embodiment, the present invention provides a method of enhancing a sensitivity of a cell to a pro-apoptotic stimulus, comprising administering to the cell a mimetic compound of the present invention. In another embodiment, the subject has received chemotherapy before receiving a compound of the present invention. In another embodiment, the subject is receiving chemotherapy. In another embodiment, the subject is administered chemotherapy simultaneously with a compound of the present invention. In another embodiment, the subject is administered chemotherapy after receiving a compound of the present invention. Each possibility represents a separate embodiment of the present invention.

In another embodiment, the present invention provides a method of enhancing an effectiveness of cancer chemotherapy, comprising administering to a cancer cell a mimetic compound of the present invention, wherein the cancer cell is a target of the cancer chemotherapy.

As provided herein, mimetic compounds of fragments of the ARTS C-terminus exhibit biological activity similar to fragments of the ARTS C terminus themselves, in both Jurkat cells and myeloma cells. Leukemia cells have been shown to exhibit loss of ARTS or reduced ARTS expression, and introduction of ARTS into leukemia cells confers ability to perform apoptosis and to respond to pro-apoptotic stimuli (International Application WO 03/013422, which is incorporated herein by reference). Thus, ARTS protein and mimetics thereof can confer to hematopoietic cancers the ability to perform apoptosis and to respond to pro-apoptotic stimuli.

In another embodiment, the present invention provides a method of inhibiting an apoptosis or a killing of a cell, comprising administering to the cell a mimetic compound of the present invention. As is known in the art, mimetic compounds that interact with a ligand of a protein often act as "dominant negatives," i.e. compounds that antagonize the activity of the protein that they resemble. In another embodiment, a mimetic compound binds to a downstream target of the protein it resembles, e.g. XIAP, without activating the signaling pathway ordinarily activated by the protein. In this embodiment, a mimetic compound of the present invention antagonizes the ability of ARTS to induce apoptosis. In another embodiment, the mimetic compound antagonizes the ability of another protein to induce apoptosis via IAP. In another embodiment, the mimetic compound antagonizes any other activity of ARTS. Each possibility represents a separate embodiment of the present invention.

In another embodiment, the present invention provides a method of treating a disease or disorder, wherein the disease or disorder comprises a lack of responsiveness of a somatic cell to a pro-apoptotic stimulus, comprising administering to the somatic cell a mimetic compound of the present invention.

In another embodiment, the disease or disorder treated by a method of the present invention is a cancer. In another embodiment, the disease or disorder is psoriasis. In another embodiment, the disease or disorder is a vitiligo. In another embodiment, the disease or disorder is an atopic dermatitis. In another embodiment, the disease or disorder is a hyper-proliferative or UV-responsive dermatosis. In another embodiment, the disease or disorder is a lymphohistiocytosis. In another embodiment, the disease or disorder is a tuberculosis infection. In another embodiment, the disease or disorder is a Bartonella infection.

In another embodiment, the disease or disorder is a breast cancer. In another embodiment, the disease or disorder is a prostate cancer. In another embodiment, the disease or disorder is a head and neck cancer. In another embodiment, the disease or disorder is an ovarian cancer. In another embodiment, the disease or disorder is a pancreatic cancer. In another embodiment, the disease or disorder is a colon cancer. In another embodiment, the disease or disorder is a glioblastoma. In another embodiment, the disease or disorder is a cervical cancer. In another embodiment, the disease or disorder is a lung cancer. In another embodiment, the disease or disorder is a gastric cancer. In another embodiment, the disease or disorder is a liposarcoma. In another embodiment, the disease or disorder is a sarcoma. In another embodiment, the disease or disorder is a carcinoma. In another embodiment, the disease or disorder is a lymphoma. In another embodiment, the disease or disorder is a hematopoietic cancer. In another embodiment, the disease or disorder is a leukemia. In another embodiment, the disease or disorder is a lymphoma. In another embodiment, the disease or disorder is a myeloma. In another embodiment, the disease or disorder is a melanoma.

"Apoptosis," refers, in another embodiment, to programmed cell death. In another embodiment, "apoptosis" refers to process of cell suicide, in which the cell shrinks and cleaves its substrates of caspases. In another embodiment, "apoptosis" is defined by the presence of an indicator thereof. In another embodiment, "apoptosis" refers to programmed cell death. Aberrations in apoptosis, in another embodiment, play a key role in the pathogenesis of many human diseases, ranging from degenerative disorders to autoimmunity and cancer. Each possibility represents a separate embodiment of the present invention.

In another embodiment, the disease or disorder comprises a decreased level of the ARTS protein, variant, or homologue thereof. In another embodiment, the disease or disorder comprises a decreased function of the ARTS protein, variant, or homologue thereof. In another embodiment, the disease or disorder comprises a decreased function of any ARTS protein known in the art. In another embodiment, the decreased level or function is an undetectable level or function. In another embodiment, the decreased level or function is a detectable but reduced level or function. In another embodiment, the decreased function is any function of the ARTS protein known in the art. Each of the above diseases represents a separate embodiment of the present invention.

In another embodiment, the decreased level or function is a result of a mutation in a coding sequence of the ARTS protein, variant, or homologue thereof. In another embodiment, the decreased level or function is a result of a modification in a coding sequence of the ARTS protein, variant, or homologue thereof. In another embodiment, the decreased level or function is a result of a mutation in a regulatory sequence of the ARTS protein, variant, or homologue thereof. In another embodiment, the decreased level or function is a result of a modification in a regulatory sequence of the ARTS protein, variant, or homologue thereof. In another embodiment, the mutation or modification in a regulatory sequence is in a promoter of the ARTS protein, variant, or homologue thereof. In another embodiment, the mutation or modification in a regulatory sequence is in an enhancer of the ARTS protein, variant, or homologue thereof. In another embodiment, the modification is affects methylation of the ARTS gene or promoter. In another embodiment, the mutation or modification results in a decrease of an amount or concentration of the ARTS protein in cells of the disease or disorder. Each possibility represents a separate embodiment of the present invention.

In another embodiment, the decreased level or function is a result of a mutation or alteration in the cell that increases degradation of the ARTS protein, variant, or homologue thereof. In another embodiment, the degradation is a ubiquitination-mediated proteasome degradation. In another embodiment, the degradation is due to another cellular method of protein degradation. Each possibility represents a separate embodiment of the present invention.

In another embodiment, a disease or disorder treated by a method of the present invention exhibits a lack of ARTS protein. In another embodiment, the disease or disorder exhibits a lack of responsiveness to a pro-apoptotic stimulus. In another embodiment, the disease or disorder exhibits a lack of ability to undergo apoptosis. In another embodiment, the disease or disorder exhibits a lack of apoptosis. In another embodiment, a cancer treated by a method of the present invention exhibits a lack of ARTS protein. In another embodiment, the cancer exhibits a lack of responsiveness to a pro-apoptotic stimulus. In another embodiment, the cancer exhibits a lack of ability to undergo apoptosis. In another embodiment, the cancer exhibits a lack of apoptosis. Each possibility represents a separate embodiment of the present invention.

In another embodiment, the disease or disorder comprises an increased level of the ARTS protein, variant, or homologue thereof. In another embodiment, the disease or disorder comprises an increased function of the ARTS protein, variant, or homologue thereof. In another embodiment, the increased level or function is a result of a mutation in a regulatory sequence of the ARTS protein, variant, or homologue thereof. In another embodiment, the increased level or function is a result of a modification in a regulatory sequence of the ARTS protein, variant, or homologue thereof. In another embodiment, the mutation or modification in a regulatory sequence is in a promoter of the ARTS protein, variant, or homologue thereof. In another embodiment, the mutation or modification in a regulatory sequence is in an enhancer of the ARTS protein, variant, or homologue thereof. In another embodiment, the modification is affects methylation of the ARTS gene or promoter. Each possibility represents a separate embodiment of the present invention.

In another embodiment, the neoplastic disease or disorder that is targeted by methods and compositions of the present invention comprises an increased level of an IAP protein, variant, or homologue thereof. In another embodiment, the neoplastic disease or disorder comprises an increased function of an IAP protein, variant, or homologue thereof. In another embodiment, administration of an ARTS protein, or mimetic or derivative thereof compensates for the increased level or function of an IAP protein, restoring the capability of apoptosis to the cell. Each possibility represents a separate embodiment of the present invention.

In another embodiment, a method of the present invention further comprises administration of a cancer chemotherapy agent other than that ARTS C-terminus or mimetic thereof. In another embodiment, the cancer chemotherapy agent is a known cancer chemotherapy agent. In another embodiment, the cancer chemotherapy agent is a leukemia chemotherapy agent. In another embodiment, the cancer chemotherapy agent is a chemotherapy agent for a hematopoietic cancer. Each possibility represents a separate embodiment of the present invention.

In another embodiment, the present invention provides a method of treating a disease or disorder, wherein the disease or disorder comprises an excessive apoptosis of a somatic cell, comprising administering to the somatic cell a mimetic compound of the present invention. In another embodiment, the disease or disorder comprises an inappropriate apoptosis of a somatic cell.

In another embodiment, the disease or disorder is a neuro-degenerative disease. In another embodiment, the disease or disorder is an ischemic injury. In another embodiment, the disease or disorder is a myelodysplasia. In another embodiment, the disease or disorder is an atherosclerosis. In another embodiment, the disease is an auto-immune disease. In another embodiment, the disease or disorder is a Crohn's disease or ulcerative colitis. In another embodiment, the disease is a cytopenia. In another embodiment, the disease is a pancreatitis. In another embodiment, the disease is a periodontitis.

In another embodiment, the neuro-degenerative disease is a Huntington's disease. In another embodiment, the neuro-degenerative disease is an amyotrophic lateral sclerosis. In another embodiment, the neuro-degenerative disease is an Alzheimer's disease. In another embodiment, the neuro-degenerative disease is a Parkinson's disease. In another embodiment, the neuro-degenerative disease is a Niemann-Pick disease. In another embodiment, the neuro-degenerative disease is any other neuro-degenerative disease known in the art.

In another embodiment, the cytopenia is a lymphopenia. In another embodiment, the cytopenia is an anemia. In another embodiment, the cytopenia is a leukopenia. In another embodiment, the cytopenia is a neutropenia. In another embodiment, the cytopenia is a thrombocytopenia. In another embodiment, the cytopenia is a pancytopenia. In another embodiment, the cytopenia is any other type of cytopenia known in the art.

Each diseases and disorder disclosed herein represents a separate embodiment of the present invention.

In another embodiment, a mimetic compound of the present invention is derived from the ARTS C terminus by incorporating 1 or more modified AA residues. In another embodiment, one or more of the termini is derivatized to include a blocking group, i.e. a chemical substituent suitable to protect and/or stabilize the N- and C-termini from undesirable degradation. In another embodiment, "undesirable degradation" refers to any type of enzymatic, chemical or biochemical breakdown of the compound at its termini which is likely to affect the function of the compound, i.e. sequential degradation of the compound at a terminal end thereof.

In another embodiment, blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino AA analogs are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkyl amino groups such as methyl amino, ethylamino, dimethylamino, diethylamino, methylethylamino and the like are examples of C-terminal blocking groups. Descarboxylated AA analogues such as agmatine are also useful C-terminal blocking groups and can be either coupled to the peptide's C-terminal residue or used in place of it. In another embodiment, the free amino and carboxyl groups at the termini are removed altogether from the peptide to yield desamino and descarboxylated forms thereof without affect on peptide activity.

In another embodiment, a mimetic compound of the present invention is derived from the ARTS C terminus by another modification. In another embodiment, such modifications include, but are not limited to, substitution of one or more of the AA in the natural L-isomeric form with D-isomeric AA. In another embodiment, the peptide includes one or more D-amino acid resides, or comprises AA that are all in the D-form. Retro-inverso forms of peptides in accordance with the present invention are also contemplated, for example, inverted peptides in which all amino acids are substituted with D-amino acid forms.

In another embodiment, mimetic compounds of the present invention are acid addition salts of the ARTS C terminus. In another embodiment, an ARTS C terminal peptide is treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide suitable for use in the invention.

In another embodiment, a mimetic compound of the present invention is produced by a process comprising the step of in vivo or in vitro chemical derivatization of an ARTS C terminal peptide, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. In another embodiment, a mimetic compound of the present invention comprises a phosphorylated AA residue, e.g., phosphotyrosine, phosphoserine, or phosphothreonine.

In another embodiment, a mimetic compound of the present invention is produced by modifying an ARTS C terminal peptide using ordinary molecular biological techniques so as to improve it resistance to proteolytic degradation or to optimize solubility properties. In another embodiment, an ARTS C terminal peptide is modified to render it more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Methods of identifying mimetic compounds are well known in the art, and are described, for example, in Song J et al, Biochem Cell Biol 76(2-3): 177-188, 1998; Vogt A et al, J Biol. Chem. 270(2): 660-4, 1995; Alexopoulos K et al, J Med Chem 47(13): 3338-52, 2004; Andronati S A et al, Curr Med Chem 11(9): 1183-211, 2004; Breslin M J et al, Bioorg Med Chem Lett 13(10): 1809-12, 2003; and WO 02/081649 ("ErbB interface peptidomimetics and methods of use thereof") in the name of Greene et al. In another embodiment, model building is used to design the mimetic compounds as described in one of the above references. In another embodiment, solubility of the mimetic compounds is optimized as described in one of the above references. Each possibility represents a separate embodiment of the present invention.

In another embodiment, the present invention provides an isolated peptide comprising a fragment of an ARTS protein, wherein the ARTS fragment is a portion of the ARTS C terminus.

In another embodiment, the isolated peptide has an AA sequence that is a portion of the AA sequence set forth in SEQ ID No: 1. In another embodiment, the isolated peptide is any portion of the ARTS C terminus disclosed herein. In another embodiment, the AA sequence of the isolated peptide is homologous to a portion of the AA sequence set forth in SEQ ID No: 1. In another embodiment, the AA sequence of the isolated peptide is a C terminal sequence of an ARTS protein homologous to the ARTS protein used to generate the isolated peptide of SEQ ID No: 1. Each possibility represents a separate embodiment of the present invention.

In another embodiment, the present invention provides a composition comprising an isolated peptide of the present invention. In another embodiment, the composition is a pharmaceutical composition. Each possibility represents a separate embodiment of the present invention.

In another embodiment, the present invention provides a recombinant protein comprising an isolated peptide of the present invention. In another embodiment, the present invention provides a recombinant protein comprising a fragment of ARTS, wherein the ARTS fragment is 27 AA or less and is entirely within the 27 C-terminal AA of ARTS. In another embodiment, the present invention provides a composition comprising the recombinant protein.

In another embodiment, the present invention provides a cell comprising an isolated peptide of the present invention. In another embodiment, the present invention provides a composition comprising the cell.

In another embodiment, the present invention provides an isolated nucleotide encoding an isolated peptide of the present invention. In another embodiment, the present invention provides a composition comprising the isolated nucleotide.

In another embodiment, the present invention provides a recombinant nucleotide comprising an isolated nucleotide of the present invention. In another embodiment, the present invention provides a recombinant nucleotide comprising an isolated nucleotide encoding a fragment of ARTS, wherein the ARTS fragment is 27 AA or less and is entirely within the 27 C-terminal AA of ARTS. In another embodiment, the present invention provides a composition comprising the recombinant nucleotide.

In another embodiment, the present invention provides a cell comprising a recombinant nucleotide of the present invention. In another embodiment, the present invention provides a composition comprising the cell.

In another embodiment, the present invention provides a method of inducing an apoptosis or a killing of a cell, comprising administering to the cell an isolated peptide of the present invention.

As provided herein, the present invention demonstrates that the ARTS C-terminus is capable of inducing apoptosis (Example 3). Thus, the ARTS C-terminus, and portions thereof, are efficacious in restoring responsiveness to apoptosis to cells that have lost or have reduced levels of the responsiveness. In another embodiment, the reduced level of responsiveness is due to reduced ARTS levels. In another embodiment, the reduced responsiveness is due to a mutation in the ARTS gene or a regulatory sequence thereof. In another embodiment, the reduced responsiveness is due to elevated levels of an IAP protein. Each possibility represents a separate embodiment of the present invention.

A cancer cell type expressing elevated levels of IAP proteins is, in another embodiment, a malt lymphoma cell. In another embodiment, the cancer cell type is a squamous cell carcinoma. In another embodiment, the cancer cell type is a melanoma. In another embodiment, the cancer cell type is any other cancer cell type known in the art. Each possibility represents a separate embodiment of the present invention.

In another embodiment, the present invention provides a method of enhancing a sensitivity of a cell to a pro-apoptotic stimulus, comprising administering to the cell an isolated peptide of the present invention.

In another embodiment, the present invention provides a method of enhancing an effectiveness of cancer chemotherapy, comprising administering to a cancer cell an isolated peptide of the present invention. In another embodiment, the cancer cell is a target of the cancer chemotherapy.

In another embodiment, the present invention provides a method of inhibiting an apoptosis or a killing of a cell, comprising administering to the cell an isolated peptide the present invention. In another embodiment, the peptide acts as a dominant negatives, thus antagonizing an activity of ARTS. In another embodiment, a peptide binds to a downstream target of the protein, e.g. XIAP, without activating the signaling pathway ordinarily activated by the protein. In this embodiment, the peptide antagonizes the ability of ARTS to induce apoptosis. In another embodiment, the peptide antagonizes the ability of another protein to induce apoptosis via IAP. In another embodiment, an isolated nucleotide of the present invention antagonizes apoptosis by inducing expression of a dominant negative ARTS C-terminal fragment. Each possibility represents a separate embodiment of the present invention.

In another embodiment, the apoptosis inhibited by a method of the present invention is induced by a pro-apoptotic stimulus. In another embodiment, the apoptosis is induced by a disease or disorder that causes or is accompanied by excessive apoptosis. In another embodiment, the apoptosis is induced by any other course of apoptosis known in the art. Each possibility represents a separate embodiment of the present invention.

Methods of assessing apoptosis as well known in the art, and include, e.g., morphological methods (Examples; Jacquel A et al, FASEB J. 2003 November; 17(14):2160-2), DNA fragmentation (Jacquel et al, ibid), expression of apoptosis-associated proteins (ibid), mitochondrial membrane depolarization (ibid), flow cyometry (McEwen A, J Pathol. 2003 November; 201(3):395-403), and Annexin-V and Propidium iodide staining (Liu J et al, Acta Med Okayama. 2003 October; 57(5):209-16). Each assay represents a separate embodiment of the present invention.

In another embodiment, the present invention provides a method of treating a disease or disorder, wherein the disease or disorder comprises a lack of responsiveness of a somatic cell to a pro-apoptotic stimulus, comprising administering to the somatic cell an isolated peptide of the present invention.

In another embodiment, the present invention provides a method of treating a disease or disorder, wherein the disease or disorder comprises an excessive apoptosis of a somatic cell, comprising administering to the somatic cell an isolated peptide of the present invention. In another embodiment, the disease or disorder comprises an inappropriate apoptosis of a somatic cell.

In another embodiment, the target cell of methods of the present invention is a cancer cell. In another embodiment, the cell is a neoplastic cell. In another embodiment, the cell is any other type of cell known in the art for which a need exists to induce apoptosis or killing thereof. In another embodiment, the cell is any other type of cell known in the art for which a need exists to reduce or inhibit apoptosis or killing thereof. Each possibility represents a separate embodiment of the present invention.

In another embodiment, the cancer cell of methods of the present invention is a hematopoetic cancer cell. In another embodiment, the cancer cell is a leukemia cell. In another embodiment, the cancer cell is a breast cancer cell. In another embodiment, the cancer cell is a prostate cancer cell. In another embodiment, the cancer cell is a head and neck cancer cell. In another embodiment, the cancer cell is an ovarian cancer cell. In another embodiment, the cancer cell is a pancreatic cancer cell. In another embodiment, the cancer cell is a colon cancer cell. In another embodiment, the cancer cell is a glioblastoma cell. In another embodiment, the cancer cell is a cervical cancer cell. In another embodiment, the cancer cell is a lung cancer cell. In another embodiment, the cancer cell is a gastric cancer cell. In another embodiment, the cancer cell is a liposarcoma cell. In another embodiment, the cancer cell is a sarcoma cell. In another embodiment, the cancer cell is a carcinoma cell. In another embodiment, the cancer cell is a lymphoma cell. In another embodiment, the cancer cell is a myeloma cell. In another embodiment, the cancer cell is a melanoma cell. In another embodiment the cancer cell is any other type of cancer cell known in the art. Each possibility represents a separate embodiment of the present invention.

In another embodiment, the present invention provides a method of inducing an apoptosis or a killing of a cell, comprising administering to the cell an isolated nucleotide of the present invention. In another embodiment, an isolated nucleotide of the present invention is taken up by a target cell, which then produces the protein encoded by the nucleotide. Thus, administration of the isolated nucleotide is a method of introducing to the cell an isolated peptide of the present invention.

In another embodiment, the present invention provides a method of enhancing a sensitivity of a cell to a pro-apoptotic stimulus, comprising administering to the cell an isolated nucleotide of the present invention.

In another embodiment, the present invention provides a method of enhancing an effectiveness of cancer chemotherapy, comprising administering to a cancer cell an isolated nucleotide of the present invention, wherein the cancer cell is a target of the cancer chemotherapy.

In another embodiment, the present invention provides a method of inhibiting an apoptosis or a killing of a cell, comprising administering to the cell an isolated nucleotide of the present invention.

In another embodiment, the present invention provides a method of treating a disease or disorder, wherein the disease or disorder comprises a lack of responsiveness of a somatic cell to a pro-apoptotic stimulus, comprising administering to the somatic cell an isolated nucleotide of the present invention.

In another embodiment, the present invention provides a method of treating a disease or disorder, wherein the disease or disorder comprises an excessive apoptosis of a somatic cell, comprising administering to the somatic cell an isolated nucleotide of the present invention. In another embodiment, the disease or disorder comprises an inappropriate apoptosis of a somatic cell.

In another embodiment, the present invention provides a mimetic compound of an isolated peptide of the present invention.

In another embodiment, the present invention provides an isolated complex comprising a C-terminal fragment of an ARTS protein and an IAP (X-link inhibitor of apoptosis) protein or a fragment of the IAP protein.

As provided herein, the present invention demonstrates that the C-terminal ARTS fragment binds to XIAP. This was determined by showing that the ARTS C-terminus peptide co-localizes with XIAP in the cytoplasm and forms a complex with XIAP in vivo (Example 2).

The C-terminal fragment of an ARTS protein in the isolated complex can be, in another embodiment, any of the embodiments of an ARTS C terminus disclosed herein.

In another embodiment, the fragment of an IAP protein corresponds to a Bir3 domain. A Bir3 domain is, in another embodiment, a domain of IAP. In another embodiment, the Bir3 domain consists of approximately AA 261-329 of XIAP. In another embodiment, the Bir3 domain consists of approximately AA 255-321 of XIAP. Each possibility represents a separate embodiment of the present invention.

In another embodiment, the present invention provides a compound that selectively binds to an isolated complex of the present invention.

In another embodiment, the present invention provides a compound that inhibits a formation of an isolated complex of the present invention.

In another embodiment, the present invention provides a compound that disrupts an isolated complex of the present invention.

In another embodiment, the compound disrupts or inhibits formation of the complex by sterically blocking interaction between the C-terminus of ARTS and the IAP protein. In another embodiment, the compound disrupts or inhibits formation of the complex by sterically blocking interaction between the C-terminus of ARTS and another component of the complex. In another embodiment, the compound disrupts or inhibits formation of the complex by sterically blocking interaction between the IAP protein and another component of the complex. In another embodiment, the compound disrupts or inhibits formation of the complex by interacting with the C-terminus of ARTS protein alone, for example by inducing a conformational change that precludes or reduces interaction with the IAP protein or another component of the complex. In another embodiment, the compound disrupts or inhibits formation of the complex by interacting with the IAP protein alone, precluding or reducing interaction with or another component of the complex. In another embodiment, the compound disrupts or inhibits formation of the complex by any other mechanism known in the art. Each possibility represents a separate embodiment of the present invention.

In another embodiment, the present invention provides a method of testing a compound for an ability to inhibit or reduce an incidence of an apoptosis, comprising determining whether the compound disrupts an isolated complex of the present invention, whereby if the compound disrupts an isolated complex of the present invention, then the compound inhibits or reduces an incidence of an apoptosis. As provided herein, isolated complexes of the present invention are pro-apoptotic. Thus, in another embodiment, disrupting the complexes is an effective means of inhibiting apoptosis. In another embodiment, promoting formation of the complexes enhances apoptosis. Each possibility represents a separate embodiment of the present invention.

In another embodiment, the present invention provides a method of treating or reducing an incidence of a disease or disorder, wherein the disease or disorder comprises an excessive apoptosis of a somatic cell, comprising contacting the somatic cell with a compound that disrupts or inhibits a formation of an isolated complex of the present invention, thereby treating or reducing an incidence of a disease or disorder. In another embodiment, the disease or disorder comprises an inappropriate apoptosis of a somatic cell.

In another embodiment, a compound utilized in a method of present invention is discovered using an in vitro assay, wherein the assay utilizes an isolated complex of the present invention. In another embodiment, the compound is tested using an in vitro assay that utilizes an isolated complex of the present invention. In another embodiment, the assay tests the ability of a compound to disrupt the isolated complex. In another embodiment, the assay tests the effect of a compound on formation of the isolated complex. In another embodiment, the assay tests the ability of a compound to bind to the isolated complex. In another embodiment, the assay is any other type of in vitro assay known in the art.

In another embodiment, the assay is performed in a recombinant cell. In another embodiment, the assay tests the ability of a compound to induce degradation of the isolated complex in the cell. In another embodiment, the assay tests the ability of a compound to induce intracellular translocation of the isolated complex in the cell. In another embodiment, the assay is any other type of cellular assay known in the art.

Each type of assay represents a separate embodiment of the present invention.

In another embodiment, the present invention provides a method of treating or reducing an incidence of a disease or disorder, wherein the disease or disorder comprises a lack of responsiveness of a somatic cell to a pro-apoptotic stimulus, comprising contacting the somatic cell with a compound that increases a stability of an isolated complex of the present invention, thereby treating or reducing an incidence of a disease or disorder.

In another embodiment, the present invention provides a method of treating or reducing an incidence of a disease or disorder, wherein the disease or disorder comprises a lack of responsiveness of a somatic cell to a pro-apoptotic stimulus, comprising contacting the somatic cell with a compound that promotes a formation of an isolated complex of the present invention, thereby treating or reducing an incidence of a disease or disorder.

In another embodiment, the present invention provides a method of enhancing an effectiveness of cancer chemotherapy, comprising administering to a cancer cell a compound that increases a stability of an isolated complex of the present invention, wherein the cancer cell is a target of the cancer chemotherapy.

In another embodiment, the present invention provides a method of enhancing an effectiveness of cancer chemotherapy, comprising administering to a cancer cell a compound that promotes a formation of an isolated complex of the present invention, wherein the cancer cell is a target of the cancer chemotherapy.

In another embodiment, the present invention provides a method of testing a compound for an ability to inhibit or reduce an apoptosis, comprising determining whether the compound inhibits a binding of a C-terminal fragment of an ARTS protein to an IAP protein, whereby if the compound inhibits binding of the C-terminal fragment of an ARTS protein to the IAP protein, then the compound inhibits or reduces an incidence of an apoptosis.

In another embodiment, the present invention provides a method of testing a compound for an ability to increase or potentiate an apoptosis, comprising determining whether the compound enhances a binding of a C-terminal fragment of an ARTS protein to an IAP protein, whereby if the compound enhances binding of the C-terminal fragment of an ARTS protein to the IAP protein, then the compound increases or potentiates an apoptosis.

In another embodiment, the present invention provides a method of testing a compound for an ability to enhance an effectiveness of a cancer chemotherapy, comprising determining whether the compound enhances a binding of a C-terminal fragment of an ARTS protein to an IAP protein, whereby if the compound enhances binding of the C-terminal fragment of an ARTS protein to the IAP protein, then the compound enhances an effectiveness of a cancer chemotherapy.

In another embodiment, the present invention provides a method of treating or reducing an incidence of a disease or disorder, wherein the disease or disorder comprises an excessive apoptosis of a somatic cell, comprising administering to the somatic cell a compound that inhibits a binding of a C-terminal fragment of an ARTS protein to an IAP protein, thereby treating or reducing an incidence of a disease or disorder. In another embodiment, the disease or disorder comprises an inappropriate apoptosis of a somatic cell.

In another embodiment, the present invention provides a method of treating or reducing an incidence of a disease or disorder, wherein the disease or disorder comprises a lack of responsiveness of a somatic cell to a pro-apoptotic stimulus, comprising administering to the somatic cell a compound that enhances a binding of a C-terminal fragment of a C-terminal fragment of an ARTS protein to an IAP protein, thereby treating or reducing an incidence of a disease or disorder.

In another embodiment, the ARTS C-terminal fragment or mimetic compound of the present invention induces apoptosis or treats one of the indicated conditions in the absence of additional pro-apoptotic stimuli. In another embodiment, the C-terminal fragment or mimetic compound induces apoptosis or treats one of the indicated conditions in combination with a pro-apoptotic stimulus. Each possibility represents a separate embodiment of the present invention.

In another embodiment, the IAP protein of methods and compositions of the present invention is an XIAP or a variant or homologue thereof. In another embodiment, the IAP protein has the sequence set forth in SEQ ID No: 5. In another embodiment, the IAP protein has a sequence homologous to the sequence set forth in SEQ ID No: 5.

(SEQ ID No: 5)
MTFNSFEGSKTCVPADINKEEEFVEEFNRLKTFANFPSGSPVSASTLARA

GFLYTGEGDTVRCFSCHAAVDRWQYGDSAVGRHRKVSPNCRFINGFYLEN

SATQSTNSGIQNGQYKVENYLGSRDHFALDRPSETHADYLLRTGQVVDIS

DTIYPRNPAMYSEEARLKSFQNWPDYAHLTPRELASAGLYYTGIGDQVQC

FCCGGKLKNWEPCDRAWSEHRRHFPNCFFVLGRNLNIRSESDAVSSDRNF

```
-continued
PNSTNLPRNPSMADYEARIFTFGTWIYSVNKEQLARAGFYALGEGDKVKC

FHCGGGLTDWKPSEDPWEQHAKWYPGCKYLLEQKGQEYINNIHLTHSLEE

CLVRTTEKTPSLTRRIDDTIFQNPMVQEAIRMGFSFKDIKKIMEEKIQIS

GSNYKSLEVLVADLVNAQKDSMQDESSQTSLQKEISTEEQLRRLQEEKLC

KICMDRNIAIVFVPCGHLVTCKQCAEAVDKCPMCYTVITFKQKIFMS.
```

The Bir3 domain used herein is the following sequence: yeariftfgtwiysvnkeqlaragfyal-gegdkvkcfhcgggltdwkpsedpweqhakwypgckyl (SEQ ID No: 6).

In another embodiment, the present invention provides methods and compositions utilizing an IAP protein other than XIAP protein. In another embodiment, the IAP protein is a CIAP protein. In another embodiment, the IAP protein is any other IAP protein known in the art. Each possibility represents a separate embodiment of the present invention.

In another embodiment, a treatment protocol of the present invention is therapeutic. In another embodiment, the protocol is prophylactic. Each possibility represents a separate embodiment of the present invention.

In another embodiment, a peptide of the present invention is homologous to a peptide disclosed herein. In another embodiment, a peptide used to design a mimetic compound of the present invention is homologous to a peptide disclosed herein. The terms "homology," "homologous," etc, when in reference to any protein or peptide, refer, in one embodiment, to a percentage of AA residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to SEQ ID No: 1 of greater than 70%. In another embodiment, "homology" refers to identity to SEQ ID No: 1 of greater than 72%. In another embodiment, "homology" refers to identity to SEQ ID No: 1 of greater than 75%. In another embodiment, "homology" refers to identity to SEQ ID No: 1 of greater than 78%. In another embodiment, "homology" refers to identity to SEQ ID No: 1 of greater than 80%. In another embodiment, "homology" refers to identity to SEQ ID No: 1 of greater than 82%. In another embodiment, "homology" refers to identity to SEQ ID No: 1 of greater than 83%. In another embodiment, "homology" refers to identity to SEQ ID No: 1 of greater than 85%. In another embodiment, "homology" refers to identity to SEQ ID No: 1 of greater than 87%. In another embodiment, "homology" refers to identity to SEQ ID No: 1 of greater than 88%. In another embodiment, "homology" refers to identity to SEQ ID No: 1 of greater than 90%. In another embodiment, "homology" refers to identity to SEQ ID No: 1 of greater than 92%. In another embodiment, "homology" refers to identity to SEQ ID No: 1 of greater than 93%. In another embodiment, "homology" refers to identity to SEQ ID No: 1 of greater than 95%. In another embodiment, "homology" refers to identity to SEQ ID No: 1 of greater than 96%. In another embodiment, "homology" refers to identity to SEQ ID No: 1 of greater than 97%. In another embodiment, "homology" refers to identity to SEQ ID No: 1 of greater than 98%. In another embodiment, "homology" refers to identity to SEQ ID No: 1 of greater than 99%. In another embodiment, "homology" refers to identity to SEQ ID No: 1 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (mRNA) and ribozymes. The use of siRNA and mRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

In one embodiment, "contacting" refers to a method of exposure, which can be direct or indirect. In another embodiment, supply to a cell is indirect, such as via administration to a subject. In another embodiment, a compound of the present invention is administered to a subject, and the compound is allowed to come in contact with the target cell in vivo. Each possibility represents a separate embodiment of the present invention.

In another embodiment of the methods of the present invention, the compound is carried in the subjects' bloodstream to the target cell. In another embodiment, the compound is carried by diffusion to the target cell. In another embodiment, the compound is carried by active transport to the target cell. In another embodiment, the compound is administered to the subject in such a way that it directly contacts the target cell. Each possibility represents a separate embodiment of the present invention.

Pharmaceutical Compositions and Methods of Administration

The compounds of the present invention and pharmaceutical compositions comprising same can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. These agents include, but are not limited to, cancer chemotherapy agents. In another embodiment, these agents are appropriate for the disease or disorder that is being treated, as is well known in the art.

EXPERIMENTAL DETAILS SECTION

Example 1

Expression of Arts C Terminus in COS-7 Cells

Materials and Experimental Methods

Subcloning of the ARTS C Terminus Construct

A construct expressing the ARTS 27 C-terminal AA (YGPSLRLLAPPGAVKGTGQEHQGQGCH, SEQ ID No: 1) containing a myc tag was produced using the following protocol:

First, the ARTS C terminus was amplified by polymerase chain reaction (PCR) using the following primers:

```
                                        (SEQ ID No: 2)
Forward primer: CGAATTCCTATGGTCCAAGCCTGA;
includes an EcoRI site followed by an
initiator codon, encoding methionine (SEQ ID No: 3)
Reverse primer: TACCGCTCGAGCTAGTGGCAGCCCTGCCC;
includes an XhoI site.
```

The gene for full-length ARTS was used as the template. PCR parameters were as follows:

Initial denaturing step: 95° C., 4 minutes (min), followed by 30 of the following cycles:

(1) 95° C., 30 seconds (sec); (2) 52° C., 30 sec; (3) 72° C., 30 sec.

Final extension: 72° C., 10 min.

The amplified DNA fragment was purified by gel electrophoresis, digested with the EcoRI and XhoI restriction enzymes, and subcloned into the EcoRI and XhoI sites of the pCS-6MT vector. The obtained vector expressed the 27 C-terminal AA of ARTS, preceded by a methionine initiator codon and a myc tag. Correct subcloning was verified by restriction analysis and sequencing.

Transfections

COS-7 cells were seeded onto a 60 mm plate. 16 hours (hr) later, the cells were transiently transfected with 5 micrograms (mcg) of DNA mixed with 9 microliters (mcL) of JetPei reagent (Polyplus-transfection, Illkirch, France).

Results

Figure 1:
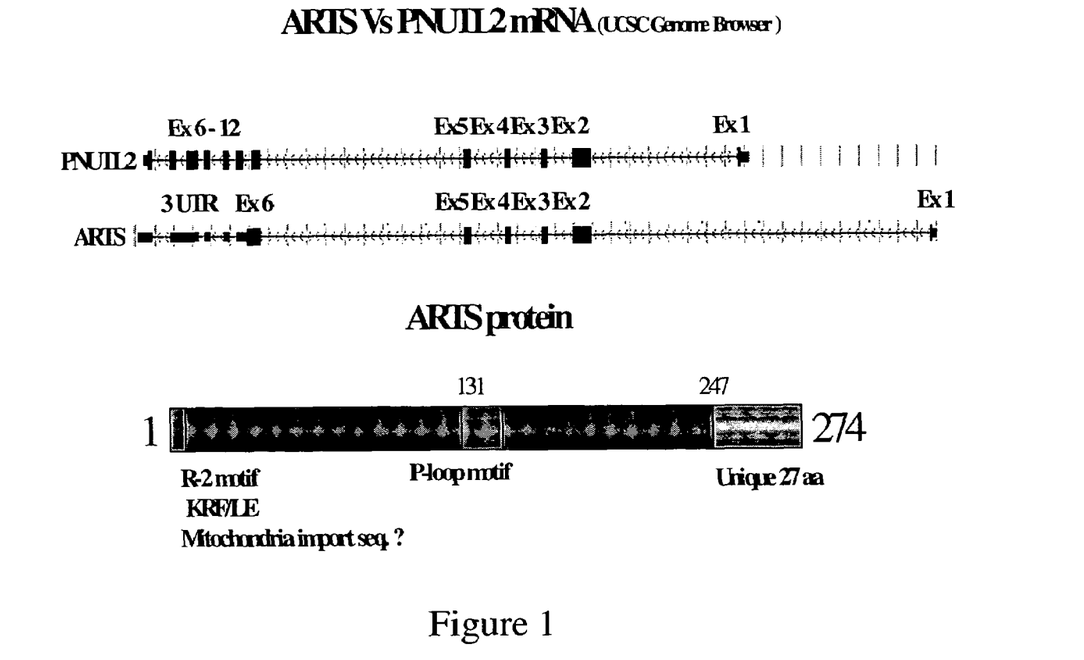
FIG. 1 depicts the structure of ARTS vs. PNUTL2.
Figure 2:
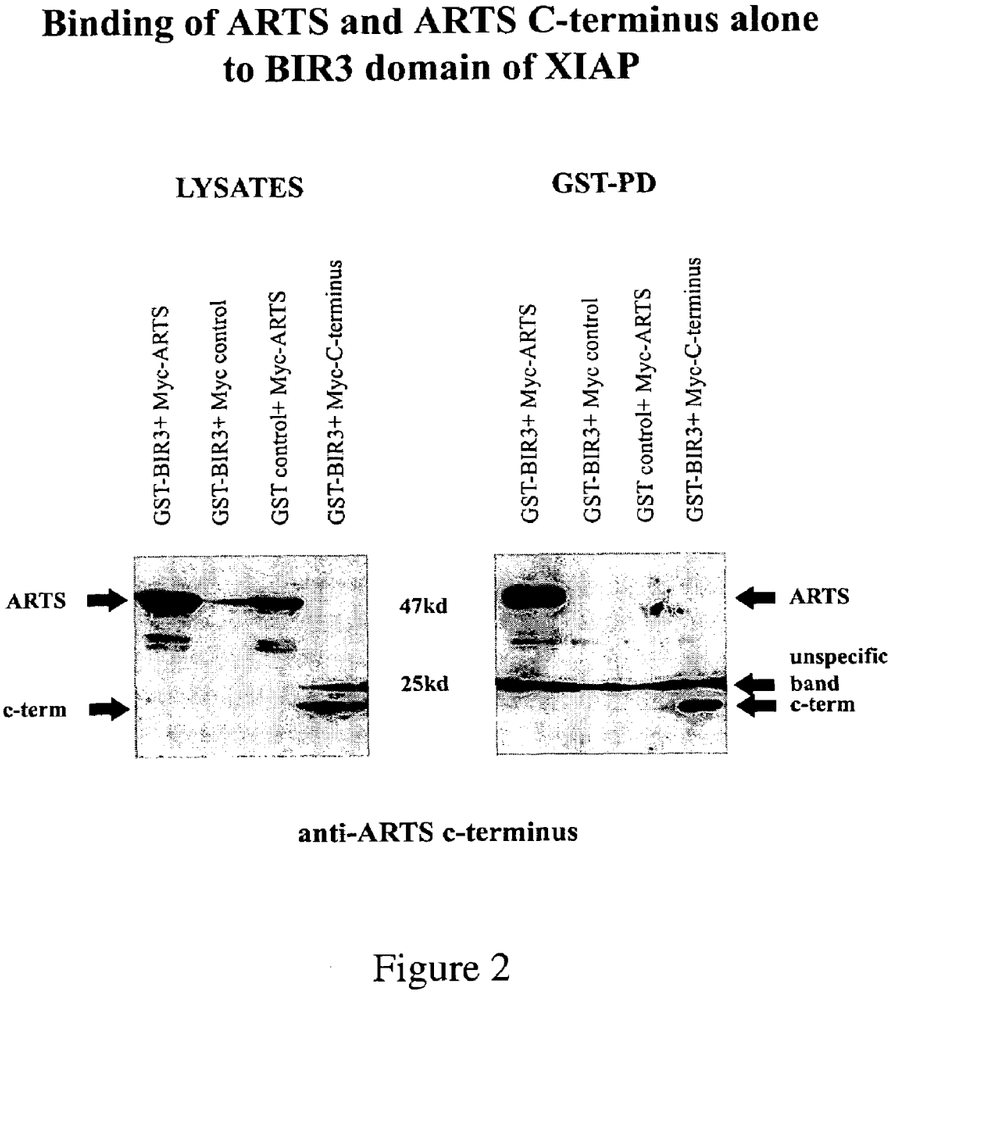
FIG. 2 shows expression of the ARTS C-terminal peptide and immunoprecipitation (IP) of the ARTS C-terminal peptide by an XIAP Bir3 domain fused to GST protein. COS-7 cells were transfected with vectors expressing either the Bir3 domain of XIAP protein fused to GST ("GST-BIR3") or GST alone ("GST control"), together with the myc-tagged ARTS C-terminus ("myc-ARTS") or myc alone ("myc control"). Expression of the ARTS C-terminus is shown by its presence in lysates (left panel; fourth lane). Interaction of the ARTS C-terminus with the Bir3 domain of XIAP is shown by its presence in samples immunoprecipitated with GST-BIR3 and glutathione beads (right panel; fourth lane). Left panel: lysates. Right panel: immunoprecipitates.

A construct expressing the 27 C-terminal AA of ARTS with a myc-tag was generated. The peptide was successfully expressed, as shown by Western blotting using an anti-ARTS monoclonal antibody raised against the ARTS C-terminus and using anti-myc antibodies (FIG. 2). Expression was further confirmed using fluorescence-activated cells sorting (FACS), using both anti-ARTS C terminus and anti-myc antibodies.

Example 2

The Arts C-Terminus Peptide Forms a Complex with the Bir3 Domain of XIAP Protein In Vivo Materials and Experimental Methods Plasmids The Bir3 domain of XIAP protein was sub-cloned into its expression plasmid using a similar strategy to that described above for the ARTS C-terminus.

Co-Immunoprecipitations

COS-7 cells were transfected with 2.5 μg each of vectors expressing either the Bir3 domain of XIAP protein fused to GST or the GST alone, together with the myc-tagged ARTS C-terminus or myc-ARTS alone. After 40 hr, cells were exposed to 1.25 μM staurosporine for 1 hr and then washed in phosphate-buffered saline (PBS), scraped off the dish, pelleted, resuspended in 20 μL lysis buffer (150 mM NaCl, 50 mM Tris-HCl (pH 8), 1% NP-40, 0.5% deoxycholate acid, protease inhibitors (Mini Complete®, Roche Applied Science, Indianapolis, Ind.), and incubated on ice for 20 min.

Lysis buffer was added to lysate containing 400 mcg total protein, to a final volume of 1 ml. 100 mcL of 20% glutathione beads was added, and the mixture was rotated at 7.5° C. overnight. Beads were centrifuged at 400×g for 2 min and washed 3 times in 1 ml RIPA buffer (0.1% SDS, 1% NP-40, 0.5% deoxycholate acid, 150 mM NaCl, 50 mM Tris-HCl (pH 8), protease inhibitors). The pellet was boiled for 5 min in an additional 25 mcL RIPA buffer and 10 mcL 4× loading buffer, then the sample was electrophoresed on an SDS poly-acrylamide gel, transferred to PVDF membrane, and subjected to Western blot using monoclonal antibody directed against the ARTS C-terminus. Blots were developed with the West Pico kit (Pierce Biotechnology, Rockford, Ill.).

Results

To directly show interaction between the ARTS C terminus and XIAP protein, the the ARTS C terminus was co-transfected into COS-7 cells with a fusion of GST and the Bir3 domain of XIAP. IP of staurosporine-treated cells with glutathione beads co-precipitated the ARTS C terminus (FIG. 2), showing that the two proteins interact in vivo.

These findings show that the ARTS C terminus mediates interaction of ARTS with XIAP protein in vivo. In addition, these findings show that Bir3 domain of XIAP protein mediates interaction with the ARTS C terminus.

Example 3

The Arts C-Terminus is Sufficient for Induction of Apoptosis

Materials and Experimental Methods

Apoptosis Assays

Cells were incubated for 24 hours with no peptide (negative control) or with 100 micromolar (mcM) peptides corresponding to residues 1-9 ("pep1"), 10-18 ("pep2"), or 19-27 ("pep3") of the ARTS C-terminus Apoptotic cells were detected using DAPI staining or TUNEL. For TUNEL assays, the cells were fixed and permeabilized. Apoptosis levels were determined using the TUNEL In situ™ cell death detection TMR kit (Roche) according to the manufacturer's protocol. All samples were coded, and experiments were performed in a blind manner.

Results

Figure 3:
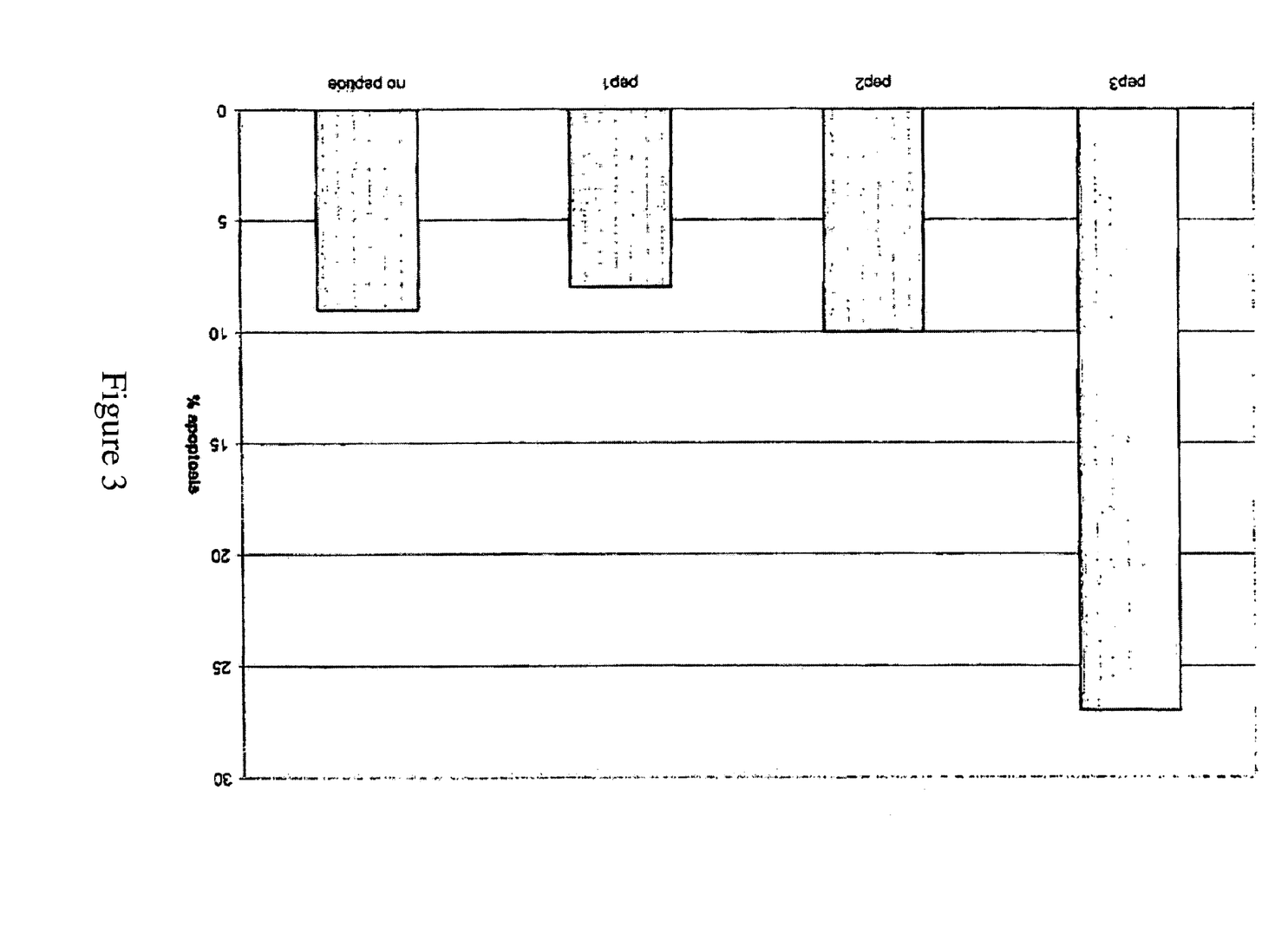
FIG. 3. 9-mer peptides derived from the ARTS C-terminus exhibit pro-apoptotic activity. Cells were incubated with no peptide ("no peptide") or with peptides corresponding to residues 1-9 ("pep1"), 10-18 ("pep2"), or 19-27 ("pep3") of the ARTS C-terminus.

The ARTS C terminus was shown to be sufficient for induction of apoptosis, and was thus further divided to define its regions with biological activity. Three fragments, pep1, pep2, and pep3 (residues 1-9, 10-18, and 19-27) were shown to penetrate cells using fluorescence of Fluorescein-labeled peptides. To determine whether these fragments were sufficient to induce apoptosis, they were added to the media of K562 cells (an erythroleukemia cell line derived from a chronic myeloid leukemia patient in blast crisis). The third peptide (residues 19-27) showed significant pro-apoptotic activity, while the second peptide (residues 10-18) showed lesser, but detectable, activity (FIG. 3).

Thus, the ARTS C terminus and fragments thereof are capable of inducing apoptosis in cells.

Example 4

Further Delineation of the Active Region(s) of the Arts C Terminus

The ARTS C terminus is further divided into segments (e.g. segments of 6, 7, 8, 9, 10, 11, 12, 13, 14, 15, 16, 17, 18, 19, 20, 21, 22, 23, 24, 25, or 26 AA long), which are used in the assays described in the above Examples, in order to further delineate the portions of the ARTS C terminus required for biological activity. Additional portions of the 27 amino acid C-terminal region are shown to possess biological activity, further delineating the regions of the C-terminal region that possess biological activity.

Example 5

Creation, Design, and Testing of Arts Protein Non-Peptide Mimetics

The biologically active region of ARTS was used as the basis for generation of an ARTS mimetic compound. The mimetic compound corresponded to residues 19-27 of the ARTS C terminus, but contained D-glutamine in place of L-glutamine. The mimetic was added to 2 different cell lines, Jurkat ALL, or acute lymphoblastic leukemia) cells and ARH-77 cells (a multiple myeloma line) at a concentration of 100 mcM for 48 hours. As depicted in Table 1, the mimetic induced apoptosis in both cell lines.

TABLE 1

| Induction of apoptosis in 2 cell lines by an ARTS C-terminus mimetic. | | |
|---|---|---|
| Cell type/condition | Background (no mimetic) | With mimetic |
| Jurkat | 22600 | 42139 |
| ARH-77 | 31500 | 39000 |

Example 6

Further Testing of Non-Peptide Mimetic Compounds of the Arts Protein C Terminus One or more ARTS protein C terminus non-peptide mimetic compounds obtained from Example 5 are tested for ability to confer sensitivity to pro-apoptotic stimuli (e.g. exposure to TGF-beta protein) in cells such as leukemia cells that have partially or completely lost such sensitivity. Alternatively or in addition, the mimetics are tested for ability to induce apoptosis in the absence of additional pro-apoptotic stimuli. If necessary, the mimetics are modified to enhance their cell membrane permeability. Mimetic compounds able to induce apoptosis are likely to have utility in treating neoplastic disorders characterized by a decreased sensitivity to pro-apoptotic stimuli (e.g. leukemia).

Next, the ARTS protein non-peptide mimetic(s) exhibiting these properties and having acceptable toxicity profiles are tested for effectiveness in an animal model of a neoplastic disorder (e.g. leukemia). Alternatively or in addition, the mimetics are tested for ability to treat the neoplastic disorder or a similar disorder in humans.

Example 7

Additional Testing of Arts Protein C Terminus Non-Peptide Mimetics

One or more ARTS protein C terminus non-peptide mimetic compounds are tested for ability to reduce sensitivity to pro-apoptotic stimuli. In this case, cell types known to be sensitive to a particular stimulus are exposed to the stimulus in the presence and absence of the mimetic. Mimetic compounds able to reduce sensitivity of cells to pro-apoptotic stimuli are likely to have utility in treating disorders characterized by inappropriate or excessive apoptosis of a somatic cell (e.g. a neuro-degenerative disease).

What is claimed is:

1. A mimetic compound of a fragment of an ARTS (Apoptosis Related Protein in the TGF-β Signaling Pathway) protein, wherein said mimetic consists of residues 19-27 (SEQ ID No. 1) of the ARTS C-terminus, wherein L-glutamine residue is replaced with a D-glutamine residue.

2. A composition comprising the mimetic compound of claim 1.

* * * * *

SEQUENCE LISTING

```
<160> NUMBER OF SEQ ID NOS: 6

<210> SEQ ID NO 1
<211> LENGTH: 27
<212> TYPE: PRT
<213> ORGANISM: Homo sapiens

<400> SEQUENCE: 1

Tyr Gly Pro Ser Leu Arg Leu Leu Ala Pro Pro Gly Ala Val Lys Gly
1               5                   10                  15

Thr Gly Gln Glu His Gln Gly Gln Gly Cys His
            20                  25

<210> SEQ ID NO 2
<211> LENGTH: 24
<212> TYPE: DNA
<213> ORGANISM: Artificial
<220> FEATURE:
<223> OTHER INFORMATION: primer

<400> SEQUENCE: 2
cgaattccta tggtccaagc ctga                                            24

<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
taccgctcga gctagtggca gccctgccc                                       29

<210> SEQ ID NO 4
<211> LENGTH: 274
<212> TYPE: PRT
<213> ORGANISM: Homo sapiens

<400> SEQUENCE: 4

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
```

```
                  20                  25                  30

Ala Lys Thr Trp Ala Ser Arg Pro Gln Val Pro Glu Pro Arg Pro Gln
        35                  40                  45

Ala Pro Asp Leu Tyr Asp Asp Leu Glu Phe Arg Pro Pro Ser Arg
50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
                100                 105                 110

Asn Gln Val His Arg Lys Ser Val Lys Lys Gly Phe Asp Phe Thr Leu
                115                 120                 125

Met Val Ala Gly Glu Ser Gly Leu Gly Lys Ser Thr Leu Val Asn Ser
                130                 135                 140

Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Ile
                165                 170                 175

Glu Glu Lys Gly Val Arg Leu Arg Leu Thr Ile Val Asp Thr Pro Gly
                180                 185                 190

Phe Gly Asp Ala Val Asn Asn Thr Glu Cys Trp Lys Pro Val Ala Glu
                195                 200                 205

Tyr Ile Asp Gln Gln Phe Glu Gln Tyr Phe Arg Asp Glu Ser Gly Leu
                210                 215                 220

Asn Arg Lys Asn Ile Gln Asp Asn Arg Val His Cys Cys Leu Tyr Phe
225                 230                 235                 240

Ile Ser Pro Phe Gly His Gly Tyr Gly Pro Ser Leu Arg Leu Leu Ala
                245                 250                 255

Pro Pro Gly Ala Val Lys Gly Thr Gly Gln Glu His Gln Gly Gln Gly
                260                 265                 270

Cys His

<210> SEQ ID NO 5
<211> LENGTH: 497
<212> TYPE: PRT
<213> ORGANISM: Homo sapiens

<400> SEQUENCE: 5

Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
                20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
                100                 105                 110

Gly Gln Tyr Lys Val Glu Asn Tyr Leu Gly Ser Arg Asp His Phe Ala
```

```
                115                 120                 125
Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
    370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Glu Lys
        435                 440                 445

Leu Cys Lys Ile Cys Met Asp Arg Asn Ile Ala Ile Val Phe Val Pro
    450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser

<210> SEQ ID NO 6
<211> LENGTH: 66
<212> TYPE: PRT
<213> ORGANISM: Homo sapiens
```

```
-continued

<400> SEQUENCE: 6

Tyr Glu Ala Arg Ile Phe Thr Phe Gly Thr Trp Ile Tyr Ser Val Asn
1               5                   10                  15

Lys Glu Gln Leu Ala Arg Ala Gly Phe Tyr Ala Leu Gly Glu Gly Asp
            20                  25                  30

Lys Val Lys Cys Phe His Cys Gly Gly Leu Thr Asp Trp Lys Pro
        35                  40                  45

Ser Glu Asp Pro Trp Glu Gln His Ala Lys Trp Tyr Pro Gly Cys Lys
    50                  55                  60

Tyr Leu
65
```